United States Patent
Wagner et al.

(10) Patent No.: US 8,678,823 B2
(45) Date of Patent: Mar. 25, 2014

(54) DENTAL CLEANSING SOLUTION (DCS) AND METHOD OF USE

(75) Inventors: Ray A. Wagner, Tucson, AZ (US); Elizabeth P. Noble, Salisbury, NC (US)

(73) Assignee: DR Products, LLC, Tucson, AZ (US)

( * ) Notice: Subject to any disclaimer, the term of this patent is extended or adjusted under 35 U.S.C. 154(b) by 1483 days.

(21) Appl. No.: 11/784,720

(22) Filed: Apr. 9, 2007

(65) Prior Publication Data

US 2007/0238071 A1   Oct. 11, 2007

Related U.S. Application Data

(60) Provisional application No. 60/790,074, filed on Apr. 7, 2006.

(51) Int. Cl.
*A61C 15/00* (2006.01)

(52) U.S. Cl.
USPC ......................................... 433/216

(58) Field of Classification Search
USPC ............................. 433/80, 216; 601/162–165
See application file for complete search history.

(56) References Cited

U.S. PATENT DOCUMENTS

| | | | |
|---|---|---|---|
| 5,009,881 A | 4/1991 | Hill et al. | |
| 6,207,138 B1 | 3/2001 | Zhang et al. | |
| 6,224,376 B1 * | 5/2001 | Cloonan et al. | 433/216 |
| 6,375,459 B1 * | 4/2002 | Kamen et al. | 433/80 |
| 6,984,377 B2 | 1/2006 | Withiam et al. | |
| 2004/0197730 A1 * | 10/2004 | Rowe et al. | 433/80 |

* cited by examiner

*Primary Examiner* — Robyn Doan
*Assistant Examiner* — Matthew Nelson

(57) ABSTRACT

A new and useful dental cleansing solution, and a method of application of the solution, is provided. The dental cleansing solution is designed to be applied by a tooth brush to the teeth of a child under the age of 2. The dental solution is fluoride free, includes a plaque inhibitor, has a viscosity that promotes wicking when applied to the bristles of a tooth brush, is palatable to children, especially children under 2 years old, and further characterized in that it does not foam when brushed onto teeth. The solution includes a carrier, a plaque inhibitor, a humectant, a preservative and a colloidal thickener. The solution may further include one or more additives that provide pH control. The solution can be applied onto the bristles of a tooth brush and is designed to wick into the bristles of the tooth brush. Moreover, the solution can be applied to other objects that may be inserted into the oral cavity of a human, particularly a child under the age of 2.

2 Claims, 4 Drawing Sheets

DENTAL CLEANSING SOLUTION (DCS) AND METHOD OF USE

RELATED APPLICATION/CLAIM OF PRIORITY

This application is related to and claims priority from provisional application Ser. No. 60/790,074, filed Apr. 7, 2006, which provisional application is incorporated by reference herein.

BACKGROUND

The present invention relates to a new and useful dental cleaning solution that can be applied to a tooth brush or other object, and used to clean teeth and gums, especially a child's teeth and gums.

Many parents struggle with the initiation of tooth brushing during the early years of their child's development. Infants and toddlers often exhibit oral aversions to tooth brushes, and tooth pastes and gels applied to the toothbrushes. These traditional oral hygiene products produce food texture sensations of viscous paste and sudsy foam that many young children find unpleasant. Children under two years old typically are unable to expectorate the residual tooth paste after brushing, swallowing it instead. If the toothpaste contains standard concentrations of fluoride (1000 ppm), and if the child repeatedly swallows the paste over time, the risk of fluorosis (staining and enamel defects) of the permanent teeth which begin to erupt at age six greatly increases. For this reason, pediatricians and pediatric dentists do not usually recommend the introduction of fluoride containing tooth paste into the child's mouth until after age two, when they are able to learn to expectorate.

Early childhood caries (tooth decay) represents a silent epidemic in our society. Forty percent of children in the industrialized world develop the dental caries infection in their baby (primary) teeth by age six. Once established, this infectious disease can spread rapidly through the child's primary dentition causing dental cavities, mouth pain, difficulty eating and sleeping, and the need for expensive and frightening dental restorations that often require the child to be sedated or anesthetized. If the infection is not brought under control, it ultimately will involve the permanent teeth, setting the child up for a lifetime of dental problems.

Early childhood caries is preventable with early and regular oral hygiene beginning as soon as the baby teeth erupt. Given that babies and many toddlers are averse to tooth brushing and the mouth feel of toothpaste, and that fluoride containing toothpastes are generally not acceptable for use under age two, it is apparent that parents and their young children require an alternative dental cleansing product that is safe, effective, and palatable.

SUMMARY OF THE PRESENT INVENTION

The present invention relates to a new and useful dental cleansing solution designed to be applied to a tooth brush or other object, particularly an object designed to be inserted into the oral cavity of a child under 2 years old, and used to clean the teeth of the child. The invention further resides in the application of such a cleansing solution to a tooth brush, or other object intended to be inserted into the oral cavity of a human, particularly a child under the age of 2.

A dental cleansing solution according to the present invention, comprises a solution that is fluoride free, includes a plaque inhibitor, has a viscosity that promotes wicking when applied to the bristles of a tooth brush, is palatable to children, especially children under the age of 2, and further characterized in that it does not foam when brushed onto teeth. In a sense, the dental cleaning solution functions as a mouth wash as well as a tooth/gum cleaning agent.

A dental cleansing solution according to the present invention preferably includes a carrier, a plaque inhibitor, a humectant, a preservative and a colloidal thickener. The solution may also include one or more additives that provide pH control.

The dental cleansing solution is applied to a tooth brush or to another type of object that may be inserted into an oral cavity, particularly the oral cavity of a child under the age of 2. When applied to a tooth brush, the solution is applied onto the bristles of a tooth brush and allowed the solution to wick into the bristles of the tooth brush. This is in contrast to a tooth paste that would normally sit on top of the bristles.

Other features of the present invention will become further apparent from the following detailed description and the accompanying drawings and exhibits.

BRIEF DESCRIPTION OF THE DRAWINGS AND EXHIBITS

Figure 3:
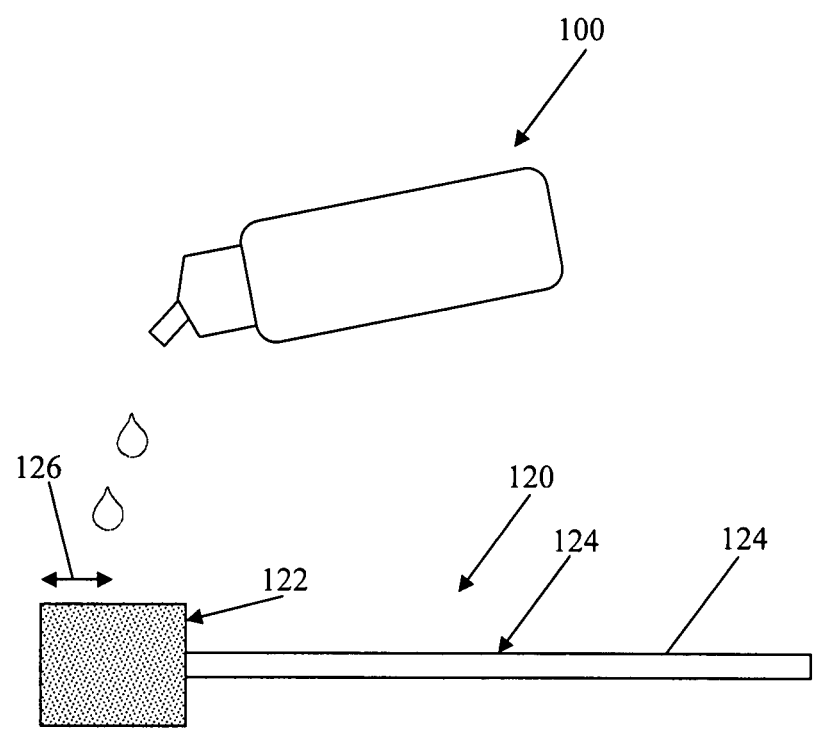
Figure 4:
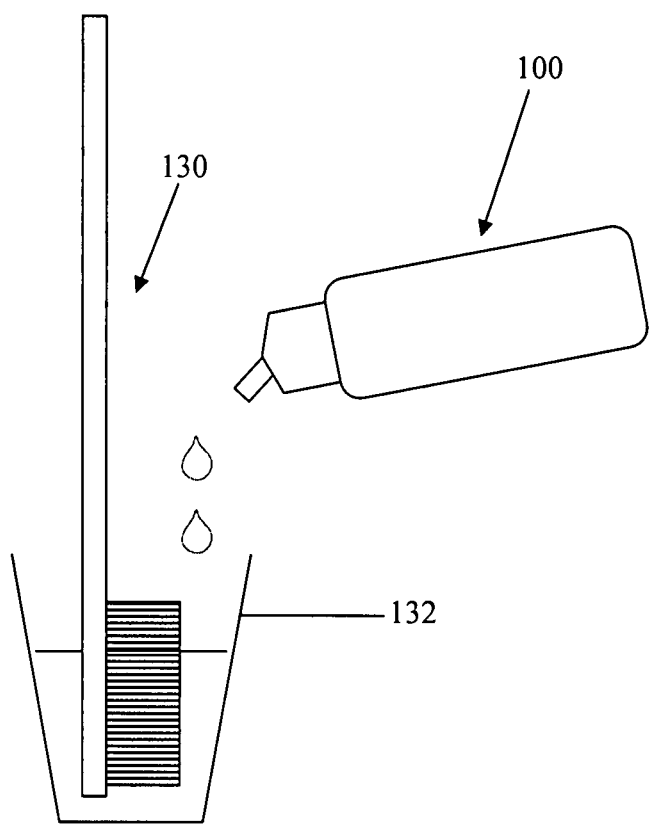

FIG. 3 is schematic illustration another type of applicator by which a dental cleansing solution can be applied to an oral cavity, particularly the oral cavity of a child under the age of 2, according to the principles of the present invention; and FIG. 4 is a schematic illustration of an alternate method of application of a dental cleansing solution by submerging the tooth brush (or another type of applicator) into a small cup or bottle cap that is partially filled with the dental cleansing solution.

Exhibit A is a color illustration of a dental cleansing solution applied to a tooth brush, according to the principles of the present invention, and exhibiting a fluid meniscus on account of the wicking of the cleansing solution onto the tooth brush; and Exhibit B is a color illustration of another form of tooth brush (known as a finger brush) that can be used to apply a dental cleansing solution to the teeth of a child, according to the principles of the present invention.

DETAILED DESCRIPTION

As discussed above, the present invention relates to a new and useful dental cleaning solution that can be applied to a tooth brush or other object, and used to clean teeth and gums, especially the teeth and gums of a child under the age of 2. The principles of the invention are described herein in connection with some exemplary dental cleansing solutions, but it will be clear to those in the art how those principles can be used to form various types of dental cleaning solutions.

Figure 1:
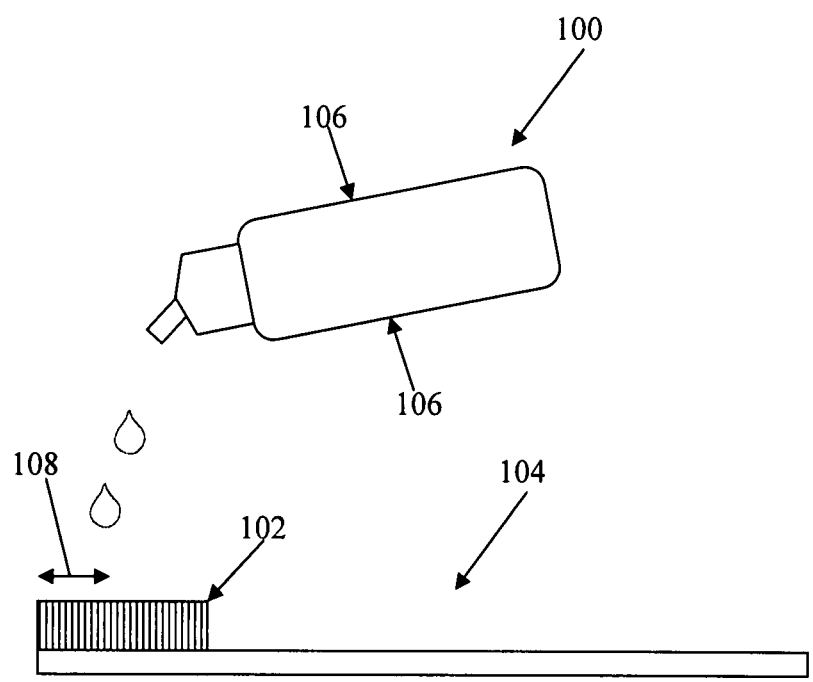
FIG. 1 is a schematic illustration of a dental cleansing solution being applied to a tooth brush, according to the principles of the present invention.

FIG. 1 schematically illustrates the application of a cleansing solution, according to the present invention, to the bristles of a tooth brush. The cleansing solution is initially contained in a bottle 100 or other type of container. The cleansing solution can be applied from the bottle 100 onto the bristles 102 of a tooth brush 104. For example, the bottle 100 may be formed of a flexible material so that squeezing the bottle, in the manner schematically illustrated by arrows 106, will cause several drops to be emitted from the bottle and onto the bristles 102 of the tooth brush 104. Moreover, the bottle can be moved over the bristles of the tooth brush, in the directions of arrows 108, to enable the cleansing solution to be applied over the full extent of the bristles (or over a selected portion of the bristles).

Figure 2:
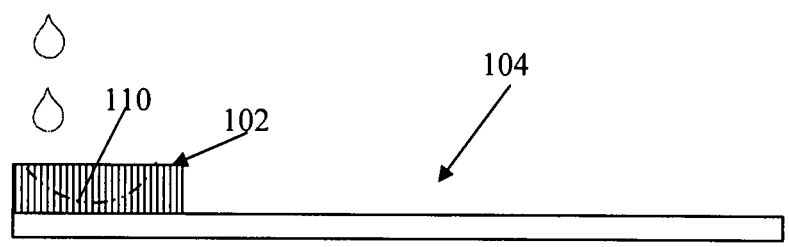
FIG. 2 is a schematic illustration of the bristles of a tooth brush, as a solution according to the present invention, is being applied to the bristles.

FIG. 2, and Exhibit A schematically illustrate the wicking of the cleansing solution into the bristles of the tooth brush. The viscosity of the cleansing solution is such that the solution, when applied to the bristles of the tooth brush, will flow along, or at least partially along the bristles, and form a meniscus along the bristles. In FIG. 2, a meniscus is schematically shown in phantom at 110. In Exhibit A, a meniscus is shown at 112.

In Exhibit B, an alternative type of tooth brush, known as an infant finger brush, is shown. Exhibit B also shows at 114 the wicking action of the dental cleansing solution onto the bristles of the infant tooth brush. In the tooth brush applicators of FIGS. 1 and 2, and Exhibits A and B, the ability of the dental cleansing solution to wick into the bristles, in the manner described and illustrated above, is one important aspect of the dental cleaning solution of the invention, as opposed to a toothpaste which would essentially set on top of the bristles. Moreover, the viscosity of the dental cleansing solution of the present invention, along with its composition that enables it to be safely swallowed effectively makes the dental cleansing solution of the present invention a form of mouthwash as well. In addition, the fact that the dental cleansing solution does not foam is also desirable, particularly for a child under the age of 2, because a solution that foams may be disagreeable to a child, especially a child under the age of 2.

FIG. 3 schematically illustrates the application of a cleansing solution, according to the present invention, to a different type of applicator 120. The cleansing solution is initially contained in and is applied from a bottle 100 or other type of container that is similar to the bottle of FIG. 1. The applicator 120 comprises a sponge like material 122 at the end of a stick 124. The applicator 120 can be of a type known as an "Oral Swab", produced by Sage Products, Cary, Ill. The length of the stick 124 is preferably such that the sponge like material 122 can reach the rear of an oral cavity, so that the dental cleansing solution can be applied to all areas of an oral cavity, including those areas toward the rear of the oral cavity.

FIG. 4 schematically illustrates another way a dental cleansing solution can be applied to an applicator, according to the principles of the present invention. An applicator such as a tooth brush 130, an applicator as shown in FIG. 3, or some other form of applicator is submerged, in whole or in part, into a small cup 132 or other receptacle such as an inverted bottle cap filled with an appropriate volume of dental cleansing solution, e.g. about 5-10 ml. of solution. The cup 132 can form a cap for the bottle 100 that holds the dental cleansing solution, and when the cup 132 is removed from the bottle 100, the dental cleansing solution can be squeezed (or poured) from the bottle 100 into the cup 132, and the applicator 130. The tooth brush or other applicator is then wholly or partially submerged in the solution, and then used to apply the solution to an oral cavity. This method of application of the dental cleansing solution to a tooth brush or other applicator is especially appealing to young children under 2 who typically have limited fine motor coordination of the hands and fingers which makes it difficult for them to correctly apply tooth paste to a tooth brush.

Set forth below are 2 examples of a dental cleansing solution, according to the principles of the present invention:

EXAMPLE 1

Dental Cleansing Solution with Grape or Apple (or Other) Flavor

A grape or apple flavored dental cleansing solution, according to the present invention, has the formula set forth in Table Y, and is manufactured by the steps set forth in Table Z.

TABLE Y

Dental Cleansing Solution

| Ingredient | Formula % | Supplier Information |
|---|---|---|
| Purified Water, USP | 58.65-73.70 | |
| Xylitol (Xylitol C) | 20.00-35.00 | Danisco, USA Inc. |
| Glycerin, USP | 5.00 | |
| Hydroxyethylcellulose (Natrosol 250 G Pharm) | 0.60 | Hercules |
| Natural Flavor (Grape, or Apple, or other) (Medallion Formulae) | 0.300-0.350 | Essential Ingredients |
| Sodium Benzoate, USP | 0.20 | |
| Trisodium Citrate Dihydrate, USP | 0.18 | Cargill |
| Citric Acid, USP | 0.07 | |

TABLE Z

Manufacturing Steps

1. Charge approximately ½ of the water into the Main Tank. Add Xylitol with moderate mixing. May be heated to 35-40 C. to speed, up dissolution of the Xylitol.
   Note: As the Xylitol dissolves, it produces an endothermic (cooling) reaction. Solution should be brought back to room temperature before the next additions are made.
2. In a separate manufacturing tank equipped with rapid agitation, charge the remaining half of the required Purified Water. Sprinkle in Hydroxyehtylcellulose using rapid agitation. Reduce mixing speed to moderate to avoid aeration. Mix until hydrated and no particles or fish eyes are seen when observed on a glass slide. Hydration time can take 1.5-2 hours. Heating gently to 35-40 C. will speed up hydration of the cellulose.
3. After Xylitol C is completely dissolved, add Glycerin and Sodium benzoate one at a time, mixing well after each addition.
4. When Hydroxyethylcellulose preparation is ready, add to Main Tank, continuing to mix until homogeneous and clear.
5. With Batch at 30 C. or below, add the Flavor. Use a portion of the Main Batch to rinse the flavor weighing container, and add the rinsing to the Main Batch. Mix until homogeneous.
6. Sprinkle the Citric Acid into the Main Tank. Continue mixing for 30-45 minutes until citric components are completely dissolved, and batch is clear and homogenous.
7. Finish: Check pH and adjust to 5.0-5.5, if needed, with Citric Acid or Trisodium Citrate

EXAMPLE 2

Dental Cleansing Solution with Grape or Apple (or Other) Flavor

TABLE Y

Dental Cleansing Solution

| Ingredient | Formula % | Supplier Information |
|---|---|---|
| Purified Water, USP | 58.65-73.70 | |
| Xylitol (Xylitol C) | 20.00-35.00 | Danisco, USA Inc. |
| Glycerin, USP | 5.00 | |
| Hydroxyethylcellulose (Natrosol 250 G Pharm) | 0.60 | Hercules |
| Natural Flavor (Grape, or Apple, or other) (Medallion Formulae) | 0.300-0.400 | Essential Ingredients |
| Sodium Benzoate, USP | ≤0.10 | |
| Trisodium Citrate Dihydrate, USP | 0.18 | Cargill |
| Citric Acid, USP | 0.07 | |
| Grapefruit seed extract (Citricidal) | 0.01-0.025 | Bio/chem. Research Inc. |

TABLE Z

Manufacturing Steps

1. Charge approximately ½ of the water into the Main Tank. Add Xylitol with moderate mixing. May be heated to 35-40 C. to speed, up dissolution of the Xylitol.
   Note: As the Xylitol dissolves, it produces an endothermic (cooling) reaction. Solution should be brought back to room temperature before the next additions are made.
2. In a separate manufacturing tank equipped with rapid agitation, charge the remaining half of the required Purified Water. Sprinkle in Hydroxyehtylcellulose using rapid agitation. Reduce mixing speed to moderate to avoid aeration. Mix until hydrated and no particles or fish eyes are seen when observed on a glass slide. Hydration time can take 1.5-2 hours. Heating gently to 35-40 C. will speed up hydration of the cellulose.
3. After Xylitol C is completely dissolved, add Glycerin, Sodium benzoate, and Grapefruit seed extract one at a time, mixing well after each addition.
4. When Hydroxyethylcellulose preparation is ready, add to Main Tank, continuing to mix until homogeneous and clear.
5. With Batch at 30 C. or below, add the Flavor. Use a portion of the Main Batch to rinse the flavor weighing container, and add the rinsing to the Main Batch. Mix until homogeneous.
6. Sprinkle the Citric Acid into the Main Tank. Continue mixing for 30-45 minutes until citric components are completely dissolved, and batch is clear and homogenous.
7. Finish: Check pH and adjust to 5.0-5.5, if needed, with Citric Acid or Trisodium Citrate Dihydrate. Take special care in adjusting the pH so that total batch content of citric/citrate does not exceed 0.30% of the total batch size. Citric/Citrate buffer is both a pH adjuster and a flavoring agent.

Note that the primary difference between the solution of example 1 and the solution of example 2 is that the sodium benzoate preservative has been reduced to ≤0.1%, and a natural food preservative, grapefruit seed extract, has been added.

In the foregoing examples, the purified water acts as a carrier; the Xylitol is a plaque inhibitor (or caries inhibitor) and flavor enhancer; the Glycerin is a humectant that, along with the Hydroxyethylcellulose, improves adherence of the solution to a tooth surface; the Hydroxyethylcellulose is a colloidal thickener that affects the texture (and mouth feel) of the solution; the natural grape or apple flavor provides a sweet flavor that is particularly palatable to a child under the age of 2; the Sodium Benzoate is a preservative and the Trisodium Citrate Dihydrate and Citric Acid provide pH control, and also provide some of the flavoring of the dental cleansing solution.

The dental cleansing solution is particularly useful for children under the age of 2. The chemical formulation of the DCS is caries (plaque) preventative without the use of fluoride, is safe and non-toxic for infants, is a sweet tasting liquid that infants and toddlers are attracted to, and is a semi-viscous liquid solution with high surface tension properties making it ideal for wicking into a tooth brush as opposed to clinging onto the top surface of a brush such as a paste or gel.

The components of the solution are all classified as food safe additives for all ages by the Food and Drug Administration. In applicants' experience, there is currently no such dental cleansing solution specifically designed and available for tooth brushing purposes.

The components of the solution are designed to make the solution as palatable as possible for a child under the age of 2. For example, the solution has a sweet flavor, which is normally the most palatable flavor for a child less than 2 years. Also, by providing a solution with a viscosity that enables it to wick into the bristles of a tooth brush (rather than sit on the bristles as with a gel), and a composition that does not foam when used to brush a child's teeth, the solution avoids two other characteristics (i.e. the feel of a gel or paste, or the feel of a foam) that, in applicants' experience are not very palatable to a child under the age of 2.

As illustrated in FIG. 3 and in Exhibit B, the dental cleansing solution according to the invention can be applied to objects other than a traditional toothbrush that may be inserted into an oral cavity, particularly the oral cavity of a child under the age of 2. For example, as illustrated in Exhibit B, the dental cleansing solution can be applied to the bristles of a child tooth brush that fits on the finger of a user, and is used to apply the dental cleansing solution to the teeth and gums of a child, particularly a child under the age of 2. Also, as illustrated in FIG. 3, the dental cleansing solution can be applied to an applicator such as the Sage Oral Swab, which has a sponge like material at the end of a stick. Moreover, as will be clear to those in the art, a dental cleansing solution according to the invention can also be applied to other objects that are inserted into the oral cavity of a child under the age of 2, e.g. a teething ring, a pacifier, a cloth that may be used to clean the teeth and gums of a child under the age of 2, etc.

With the foregoing disclosure in mind, various additional applications of the principles of the present invention will be apparent to those in the art.

The invention claimed is:

1. A method of applying a dental cleansing solution to an applicator designed to be inserted into an oral cavity of a human patient, comprising
   (a) providing a solution that is fluoride free, includes a plaque inhibitor, has a viscosity that promotes wicking when applied to a portion of an applicator that is configured to contact the teeth of a human patient, is palatable to children under the age of 2, and further characterized in that it does not foam when applied onto the teeth of a human patient by contact between the portion of the applicator and the teeth of the human patient, and
   (b) applying the solution to the portion of an applicator that is designed to be inserted into an oral cavity of a human patient and to contact the teeth of the human patient to apply the solution to the teeth of the human patient;
   (c) wherein the applicator is a child tooth brush designed to be inserted into the oral cavity of a child under the age of 2, and wherein the step of applying the solution to the portion of an applicator comprises pouring or dropping the solution into a receptacle and submerging the portion of the applicator in the solution in the receptacle.

2. A method of applying a dental cleansing solution to an applicator designed to be inserted into an oral cavity of a human patient, comprising
   (a) providing a solution that is fluoride free, includes a plaque inhibitor, has a viscosity that promotes wicking when applied to a portion of an applicator that is configured to contact the teeth of a human patient, is palatable to children under the age of 2, and further characterized in that it does not foam when applied onto the teeth of a human patient by contact between the portion of the applicator and the teeth of the human patient, and
   (b) applying the solution to the portion of an applicator that is designed to be inserted into an oral cavity of a human patient and to contact the teeth of the human patient to apply the solution to the teeth of the human patient;
   (c) wherein the applicator is a child tooth brush designed to be inserted into the oral cavity of a child under the age of 2, and wherein the step of applying the solution to the portion of an applicator comprises pouring or dropping the solution from the container onto the portion of the applicator, and allowing the solution to wick into the portion of the applicator.

* * * * *